US009616071B2

(12) United States Patent
Salle et al.

(10) Patent No.: US 9,616,071 B2
(45) Date of Patent: Apr. 11, 2017

(54) ORAL SUSTAINED RELEASE PHARMACEUTICAL COMPOSITION

(75) Inventors: Sandrine Salle, Saint Illiers la Ville (FR); Emmanuel Guerin, Colombes (FR)

(73) Assignees: ETHYPHARM (FR); TORAY INDUSTRIES, INC. (JP)

( * ) Notice: Subject to any disclaimer, the term of this patent is extended or adjusted under 35 U.S.C. 154(b) by 1142 days.

(21) Appl. No.: 10/556,641

(22) PCT Filed: May 19, 2004

(86) PCT No.: PCT/IB2004/001912
§ 371 (c)(1),
(2), (4) Date: Nov. 6, 2006

(87) PCT Pub. No.: WO2004/103350
PCT Pub. Date: Dec. 2, 2004

(65) Prior Publication Data
US 2007/0269506 A1    Nov. 22, 2007

(51) Int. Cl.
*A61K 31/5585* (2006.01)
*A61K 9/50* (2006.01)
(52) U.S. Cl.
CPC ........ *A61K 31/5585* (2013.01); *A61K 9/5078* (2013.01)
(58) Field of Classification Search
None
See application file for complete search history.

(56) References Cited

U.S. PATENT DOCUMENTS

| | | | | |
|---|---|---|---|---|
| 5,068,112 A | * | 11/1991 | Samejima et al. | 424/495 |
| 5,405,617 A | * | 4/1995 | Gowan et al. | 424/464 |
| 5,498,447 A | * | 3/1996 | Nishii et al. | 427/213 |
| 5,837,291 A | * | 11/1998 | Maruyama et al. | 424/489 |
| 6,656,502 B1 | | 12/2003 | Hara et al. | |
| 2001/0003588 A1 | * | 6/2001 | Sauer | A61K 9/1617 424/451 |
| 2002/0047058 A1 | * | 4/2002 | Verhoff | A61K 9/14 241/26 |

(Continued)

FOREIGN PATENT DOCUMENTS

| | | |
|---|---|---|
| DE | 198 08 634 A1 | 8/1999 |
| JP | 59020219 A * | 2/1984 |

(Continued)

OTHER PUBLICATIONS

CAS English abstract of JP 02-225416A (1990).*

(Continued)

*Primary Examiner* — Nissa Westerberg
(74) *Attorney, Agent, or Firm* — Lerner, David, Littenberg, Krumholz & Mentlik, LLP

(57) ABSTRACT

An oral sustained release pharmaceutical composition comprising a plurality of granules having diameters of not more than 1000 μm, wherein each of the granules comprise a nucleus granule comprised of beraprost sodium and a coating agent coating the nucleus granule, and wherein the coating agent is comprised of a first skin layer containing one or more relatively water-insoluble macromolecular substances, and a second skin layer containing one or more hot-melt low-melting substances.

4 Claims, 4 Drawing Sheets

(56) References Cited

U.S. PATENT DOCUMENTS

| | | | | |
|---|---|---|---|---|
| 2003/0147948 A1* | 8/2003 | Shinoda | ............... | A61K 9/0056 |
| | | | | 424/465 |
| 2003/0165565 A1* | 9/2003 | Mehta | ................. | A61K 31/554 |
| | | | | 424/468 |
| 2003/0198670 A1* | 10/2003 | Kumbhani | ........... | A61K 9/2054 |
| | | | | 424/468 |

FOREIGN PATENT DOCUMENTS

| | | | |
|---|---|---|---|
| JP | 01287021 A | * | 11/1989 |
| JP | 02225416 A | * | 9/1990 |
| JP | 7-145056 A | | 6/1995 |
| JP | 2000-103732 A | | 4/2000 |

OTHER PUBLICATIONS

English translation of Hara et al. (JP 02225416), original publication date Sep. 1990.*
Derwent abstract of JP 01287021.*
CAPLUS abstract of JP59020219.*
Complete translation of Kokubo et al., JP 01-87021 A, Orginal document published Nov. 1989.*
International Search Report issued on Oct. 27, 2004 in connection with corresponding International Appln. No. PCT/IB2004/001912.
Sandberg, et al., "Influence of Dissolution Rate on the Extent of Rate of Bioavailability of Metoprolol," International Journal of Pharmaceutics, vol. 68, 1991, pp. 167-177.
Korsmeyer, et al., "Mechanisms of Solute Release from Porous Hydrophilic Polymers," International Journal of Pharmaceutics, vol. 15, 1983, pp. 25-35.
Lauwo, et al., Some Pharmaceutical Studies on Sustained Release Coprecipitates of Ampicillin Trihydrate with Acrylic Resin (Eudragit(R)-RS), Drug Development and Industrial Pharmacy, vol. 16, No. 8, 1990, pp. 1375-1389.
Dahl, et al., "Influence of Physico-Chemical Properties of Hydroxypropyl Methylcellulose on Naproxen Release from Sustained Release Matrix Tablets," Journal of Controlled Release, vol. 14, 1990, pp. 1-10.
ASTM D6090-99(2008) Standard Test Method for Softening Point Resins, (2008).
Albers, Jessica et.al., "EUDRAGIT Application Guidelines", Evonik Industries AG, 12th Edition, Germany.
Ishii, Tatsuya, "Sustained Release Formulations with EUDRAGIT", Health Care/Evonik Japan, May 2016.

* cited by examiner

ORAL SUSTAINED RELEASE PHARMACEUTICAL COMPOSITION

CROSS-REFERENCE TO RELATED APPLICATIONS

The present application is a national stage application under 35 U.S.C. §371 of International Application No. PCT/IB2004/001912, filed May 19, 2004, which claims priority from European Patent Office Application No. 03291180.2, filed May 20, 2003.

The present invention relates to a pharmaceutical composition containing beraprost sodium as an effective ingredient, which regulates the release of beraprost sodium from the composition so as to give stable sustained release of beraprost sodium.

PRIOR ART

Beraprost sodium is a chemically stable prostaglandin I hereinafter referred to as "PGI" for short) derivative, and has a strong inhibition action of agglutination of platelets and strong vasodilator action. It is used for various diseases such as peripheral circulatory disturbance, and its pharmacological effects thereof are wide.

On the other hand, studies on sustained release preparations are now actively being made for other drugs too. Especially, studies aiming at sustained release of drugs having short biological half lives when administered, or reducing side effects of drugs which likely exhibit side effects in Cmax-dependent manner, or at improving compliance by decreasing the number of times of administration are being made.

Known sustained release preparations include sustained release hydro gel preparations using water-soluble macromolecules as matrices for sustained release, sustained release matrix preparations using hydrophobic macromolecules, sustained release granules using hydrophobic skins, and the like, and a method for attaining sustained release suitable for the respective drug is employed (Int. J. Pharm., 15 (1983) 25-35; J. Controlled Release, 14 (1990) 1-10; Drug Develo. Ind. Pharm., 16 (1990) 1375-1389; Int. J. Pharm., 68 (1991) 167-177; Japanese Laid-open Patent Application (Kokai) No. 7-145056; Japanese-Laid Open International Patent Application (Kohyo) No. 2001-515030; and Japanese Laid-open Patent Application (Kokai). No. 2000-103732).

The biological half life of beraprost sodium is very short. Therefore, in order to maintain the pharmacological effect by administering an ordinary preparation (injection solution, oral drug or topical drug), the drug must be frequently administered in one day. Thus, recently, to keep the pharmacological effect, decreasing the side effect and improving the compliance, research and development of oral sustained release preparation are now being made (WO98/41210 and Japanese Laid-open Patent Application (Kokai) No. 2-225416).

PROBLEMS WHICH THE INVENTION TRIES TO SOLVE

However, due to the problems on the release stability of the drug in the digestive tract, on the fact that the content of beraprost sodium in a preparation is as small as 1 mg or less, and so on, a preparation obtained by applying a known technique for attaining sustained release does not have satisfactory sustained release characteristics.

Moreover, since beraprost sodium has an extremely strong pharmacological activity, it exhibits pharmacological effects and side effects with a very small amount. Therefore, to continuously express the pharmacological effects and to avoid side effects, more precise control of the amount of the released drug is necessary than required for other drugs. However, by the ordinary techniques for attaining sustained release, the rate of release of the drug is likely to fluctuate due to the fluctuation in the amount of the digestive juice and in pH depending on the location of the drug in the digestive tract, so that distribution of the blood level of the drug is likely to be large between individuals and between locations in one individual. Especially, sustained release tablets vary in the mobility in the digestive tract and the release of the drug is likely to be influenced by the movement of the digestive tract and by the meal. Therefore, there are concerns about fluctuation of blood level, decrease in availability ratio, and shortening of the duration in which the pharmacological effects are kept. Thus, an oral sustained release preparation which gives stable release and absorption of the drug throughout the entire digestive tract is demanded. To overcome these problems, it is now tried to design a sustained release preparation as proposed in WO 98/41210, in which a hydro gel polymer that swells upon absorbing water is used as the base, so as to keep sufficient release and absorption even at the lower site of the digestive tract. However, the advantageous effect is expected only for tablets, influence by meal is concerned, and the degree of control of the release for attaining stable release is limited.

Japanese Laid-open Patent Application (Kokai) No. 2-225416 discloses to attain sustained release by combining a PGI derivative with an enteric material or with a water-insoluble material. However, it is difficult to attain sufficient sustained release property by mere kneading or coating of the PGI derivative with the enteric material or the water-insoluble material. For example, very small difference in the amount of the coated material largely influences on the release rate of the drug, so that it was difficult to keep a stable rate of release continuously.

MEANS FOR SOLVING THE PROBLEMS

The present inventors intensively studied for solving the problems to discover that a sustained release preparation having stable drug-releasing and absorbing properties of which fluctuation depending on the location in the entire digestive tract is small, i.e said release being independent of the pH of the digestive tract, which preparation is excellent in duration and bioavailability (complete release of the drug), may be obtained by designing an oral sustained release preparation comprising a plurality of granules having diameters of not more than 1000 μm, each of which comprises a nucleus granule containing beraprost sodium, and a coating agent constituting at least two skin layers including (1) a skin layer containing a relatively water-insoluble macromolecular substance and (2) a skin layer containing a hot-melt low-melting substance, the nucleus granule being coated with the coating agent.

That is, the present invention provides an oral sustained release pharmaceutical composition comprising a plurality of granules having diameters of not more than 1000 μm, each of which comprises a nucleus granule containing beraprost sodium, and a coating agent constituting at least two skin layers including (1) a skin layer containing a relatively water-insoluble macromolecular substance and (2) a skin layer containing a hot-melt low-melting substance, the nucleus granule being coated with the coating agent.

The content of beraprost sodium in the pharmaceutical composition according to the present invention may be any amount as long as a therapeutic effect is obtained, and may be, for example, 0.1 to 50,000 µg/preparation, more preferably 1 to 1000 µg preparation, still more preferably 10 to 500 µg/preparation.

In the present invention, the relatively water-insoluble macromolecular substance constituting the skin layer is a water-insoluble macromolecular substance having skin layer-forming property and ability to control the release of the drug. The coating method and the additives are not restricted. Examples of the relatively water-insoluble macromolecular substance include water-insoluble alkyl cellulose ether derivatives (e.g., ethyl celluloses, butyl celluloses, polyvinyl acetates), water-insoluble vinyl derivatives (e.g., polyvinyl butyrates) and water-insoluble acrylic polymer derivatives (e.g., acrylic acid-methacrylic acid copolymers), and mixtures of two or more of these. Preferred relatively water-insoluble macromolecular substances are acrylic acid-methacrylic acid copolymers.

The hot-melt low-melting substance constituting the skin layer is a hot-melt substance having a relatively low melting point, preferably a melting point of not higher than 70° C., more preferably from room temperature to 70° C., and ability to control the release of the drug. The coating method and the additives are not restricted. Examples of the hot-melt low-melting substance include higher fatty acids (e.g., stearic acid, capric acid, lauric acid, myristic acid and palmitic acid), higher alcohols (e.g., stearyl alcohol, myristyl alcohol, lauryl alcohol and cetyl alcohol), higher fatty acid glycerin esters (e.g., glyceryl palmitooleate, glyceryl monooleate, glyceryl monostearate, glyceryl monomyristate, glyceryl monobehenate, glyceryl trimyristate and glyceryl tribehenate), waxes (e.g., carnauba wax), saturated hydrocarbons (e.g., paraffins), and mixtures of two or more of these. Preferred examples of the hot-melt low-melting substance include cetyl alcohol, stearic acid, glyceryl palmitooleate, glyceryl monooleate, glyceryl monostearate, glyceryl monomyristate, glyceryl monobehenate, glyceryl tristearate, glyceryl trimyristate and glyceryl tribehenate.

The weight ratio of (1) the skin layer containing a relatively water-insoluble macromolecular substance and (2) the skin layer containing a hot-melt low-melting substance in the skin layers, as well as the coverage ratio of the skin; layers in the granule, is not restricted, and may be appropriately selected depending on the drug used, effective dose and the like. Usually, the ratio may be within the range of 1:9 to 9:1, preferably 3:7 to 7:3.

The skin layers in the pharmaceutical composition according to the present invention may contain pharmaceutically acceptable additives. Examples of the additives include plasticizers such as propylene glycol, polyethylene glycol (hereinafter referred to as "PEG" for short) 1500, PEG4000, PEG6000, PEG20,000, polyoxyethylenepolyoxypropylene glycols (PEP101™, PLURONIC™), glycerin, triethyl citrate, tributyl citrate, triacetin, sodium lauryl sulfate, polyoxyethylenepolyoxypropylene glycol (PEP101™, PLURONIC™), glycerin, sorbitol, polyvinylpyrrolidone and Polysorbate 80. The required amount of the plasticizer varies depending on the type of the compound used. The effective amounts of the commercially available pharmaceutical plasticizers vary within the range of 1 to 30% based on the total dry weight of the coating materials.

Examples of brittleness-inducing agent which is an additive for decreasing elasticity of the film constituting the coating include talc, magnesium stearate, calcium stearate and aerosil titanium oxide. The effective amount of the brittleness-inducing agent varies depending on the type of the brittleness-inducing agent used. For example, the effective amount of talc is 10% to 70%, that of aerosil is 1 to 40%, and that of magnesium stearate is 1 to 70%, all % herein being based on the total dry weight of the coating materials.

Additives which may be blended in the nucleus granule containing the beraprost sodium are not restricted as long as they are pharmaceutically acceptable.

Additives which are preferred include binders, vehicles, stabilizers, solubilizers or buffering agents.

Examples of binder include hydroxypropyl celluloses, hydroxypropylmethyl celluloses, methyl celluloses, stearic acid and propylene glycol. Examples of vehicles include lactose, saccharose, sucrose, D-mannitol, sorbitol, xylitol, crystalline cellulose, corn starch, gelatin, polyvinylpyrrolidone, dextran, PEG-1500, PEG-4000, PEG-6000, PEG-20000 and polyoxyethylenepolyoxypropylene glycols (PEP101™, PLURONIC™). The nucleus granule containing beraprost sodium may be prepared by coating a conventional neutral sphere such as NONPAREIL™ (saccharose), SUGLETS™ (saccharose) or ETISPHERES™ (crystalline cellulose) with the pharmaceutical active substance together with a binder. Alternatively, the nucleus granule containing beraprost sodium may be prepared by mixing beraprost sodium with a vehicle and granulating the mixture. Examples of stabilizer include butylhydroxytoluene, butylhydroxy anisole, ascorbic acid, propyl gallate, dibutylmethylphenol, sodium thiosulfate and titanium oxide. The effective amount varies depending on the pharmaceutical active substance. Examples of solubilizer include cyclodextrin, polyethylene-hardened castor oil, polyethylene glycol monostearate, poloxamer and Polysorbate 80. The effective amount varies depending on the pharmaceutical active substance. Examples of buffering agents include alkaline reacting agents, such as MgO, or acidic reacting agents, for example organic acids, such as citric acid, or tartaric acid.

In the present invention, the diameter of the granule is not more than 1000 µm, preferably 100 to 850 µm, more preferably 300 to 750 µm.

The sustained release preparation according to the present invention is constituted by a plurality of granules having diameters of not more than 1000 µm, each of which has sustained release property. By controlling the particle size of the granule to the above-mentioned range, stable release at the lower part of the digestive tract may be maintained. The final form of the preparation is not restricted, and may be, for example, tablets, granules, grains, capsules, suspensions or the like, which may be orally administered.

The preparation according to the present invention may be administered to both human and animals.

Typical uses of the oral sustained release pharmaceutical composition according to the present invention are those for which sustained effectiveness of the active substance is desired, such as vasodilators, anti-platelet agents, antiasthmatics (bronchodilators), antiemetic drugs, cardiac stimulants, analgesics, anti-inflammatory agents, antiulcer agents, antirheumatic drugs, abirritants, antidepressants, drugs for angina pectoris and hypotensive drugs.

The preparation according to the present invention is stable and has good sustained releasing property. Therefore, by orally administering the preparation once or twice a day, stable pharmacological effects is obtained for a long period of time, excellent bioavailability is obtained, and administration is easy.

EXAMPLES

Figure 1:
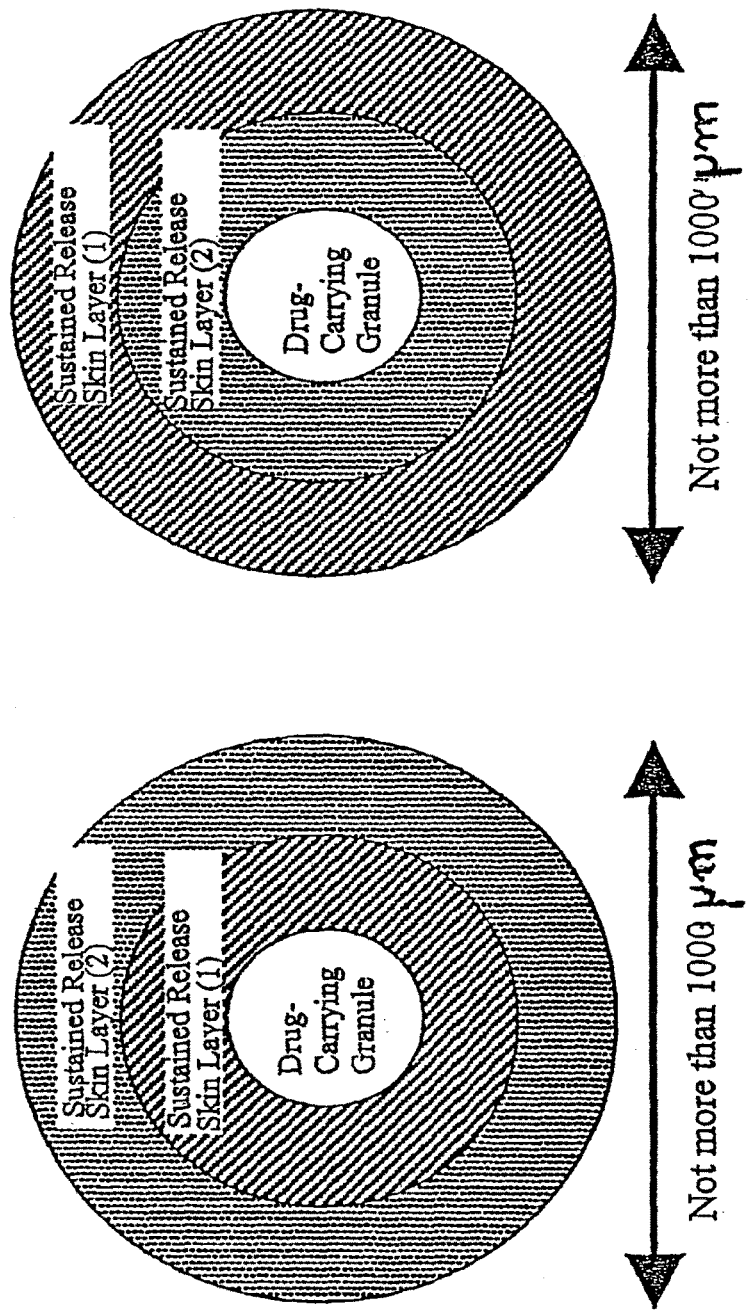
FIG. 1 is a drawing showing an embodiment of the constitution of the oral sustained release pharmaceutical composition. Sustained Release Skin Layer (1): Hot-melt Low Melting Substance. Sustained Release Skin Layer (2): Relatively Water-insoluble Macromolecular Substance.

The present invention will now be described in more detail by way of Examples, Comparative Examples, tables 1 to 4 and FIGS. 1 to 4. It should be noted that the present invention is not limited by these examples.

Table 1 shows compositions and constitutions of Formulation Examples 1 to 15.

Table 2 shows compositions and constitutions of Formulation Examples 16 to 18.

Table 3 shows compositions and constitutions of Comparative Examples 1 and 2.

Table 4 shows drug kinetic parameters when the preparations according to Comparative Examples 1 and 2, and Formulation Example 16 were orally administered.

Example 1

Preparations were prepared by the Preparation Methods 1 to 4 described below, using the components shown in Tables 1, 2 and 3 below.

Preparation Method 1

Using a centrifugal fluidization type coating apparatus, the following coating operations were carried out.

1. Drug-Carrying Step:

Spherical granular microcrystalline cellulose (ETHISPHERES™, 500-710 µm) was coated with an aqueous solution dissolving beraprost sodium, PEG-6000 and HPMC2910 by spray-coating, thereby making the granules carry the drug.

First Layer Step (Film of Hot-Melt Low-Melting Substance)

A hot-melt low-melting substance and talc were heated to melt, and coating was carried out.

Second Layer Step (Film of Relatively Water-Insoluble Macromolecular Substance)

The outermost layer was coated with an aqueous solution containing a relatively water-insoluble macromolecular substance, talc and Polysorbate 80, having the actual weight to be coated.

2. Aging Step:

Curing at 40° C. for 1 day was carried out to form films, and then talc was dispersed to obtain sustained release granules.

3. Encapsulation Step:

To each No. 2 capsule, the sustained release granules carrying 120 µg of beraprost sodium were encapsulated, thereby obtaining preparations according to Formulation Examples 1 to 15 as shown in Table 1.

Preparation Method 2

Using a centrifugal fluidization type coating apparatus, the following coating operations were carried out.

1. Drug-Carrying Step:

Neutral spheres (SUGLETS™, 500-600 µm) were coated with an aqueous solution dissolving beraprost sodium, PEG4000 and Poloxamer 188 (Lutrol™ F68) by spray-coating, thereby making the granules carry the drug.

First Layer Step (Barrier)

The granules were subjected to protective coating with an aqueous solution of HPMC603 (Pharmacoat™ 603) and talc.

Second Layer Step (Film of Hot-Melt Low-Melting Substance)

Glyceryl palmitostearate (Preciol™ ATO5) which is a hot-melt low-melting substance and talc were heated to melt, and coating was carried out.

Third Layer Step (Film of Relatively Water-Insoluble Macromolecular Substance)

The outermost layer was coated with an aqueous solution containing Eudragit™ RS30D "(poly(ethylacrylate, methlmethacrylate) trimethylammonio-ethylmethacrylate chloride, Mw 150,000)" which is a relatively water-insoluble macromolecular substance, talc, acetylated monoglyceride (Myvacet™ 9.45) and Polysorbate 80, having the actual weight to be coated.

2. Aging Step:

Curing at 40° C. for 1 day was carried out to form films, and then talc was dispersed to obtain sustained release granules.

3. Encapsulation Step:

To each No. 2 capsule, the sustained release granules carrying 120 µg of beraprost sodium were encapsulated, thereby obtaining preparations according to Formulation Examples 16 to 18 as shown in Table 2.

Comparative Examples

Preparation Method 3

Using a centrifugal fluidization type coating apparatus, the following coating operations were carried out.

1. Drug-Carrying Step:

Neutral spheres (Nonpareil™) were coated with an aqueous solution dissolving beraprost sodium and HPMC by spray-coating, thereby making the granules carry the drug.

2. Encapsulation Step:

To each No. 2 capsule, the immediate release granules carrying 120 µg of beraprost sodium were encapsulated, thereby obtaining a preparation according to Comparative Example 1 (see Table 3).

Preparation Method 4

Using a centrifugal fluidization type coating apparatus, the following coating operations were carried out.

1. Drug-Carrying Step:

Neutral spheres (Nonpareil™, 1000-1180 µm) were coated with an aqueous solution dissolving beraprost sodium, PEG-6000 and HPMC2910 by spray-coating, thereby making the granules carry the drug.

First Layer Step (Film of Relatively Water-Insoluble Macromolecular Substance)

The granules were coated with an aqueous solution containing Eudragit™ RS-100, "(poly(ethylacrylate, methylmethacrylate) trimethylammonio-ethylmethacrylate chloride, Mw 150,000)", Eudragit™ RS-100L, "(poly(ethylacrylate, methylmethacrylate) trimethylammonio-ethylmethacrylate chloride, Mw 150,000)", triethyl citrate and talc, having the actual weights to be coated, thereby forming a layer containing a water-insoluble macromolecular substance.

2. Aging Step:

Curing at 40° C. for 1 day was carried out to form a film, and then talc was dispersed to obtain sustained release granules.

3. Encapsulation Step:

To each No. 2 capsule, the sustained release granules carrying 120 µg of beraprost sodium were encapsulated, thereby obtaining a preparation according to Comparative Example 2 (See Table 3)

Test Example 1

Dissolution Test: Evaluation of Influence by pH of Testing Medium on Drug Release Method for Dissolution Test To study the influence by the pH of the testing medium, release of the drug was evaluated by the paddle method of dissolution test in the Japanese Pharmacopoeia using the first fluid and the second fluid of the disintegration test described in Japanese Pharmacopoeia The concentration of the drug released into the testing medium was measured by HPLC (fluorescence method).

Conditions of Dissolution Test: Paddle Method

Revolution of Paddle: 100 rpm; Testing Medium: the first fluid (pH 1.2) and the second fluid (pH 6.8) of the disintegration test described in Japanese Pharmacopoeia; Volume of Medium: 500 ml; Temperature: 37oC Results.

Figure 2:
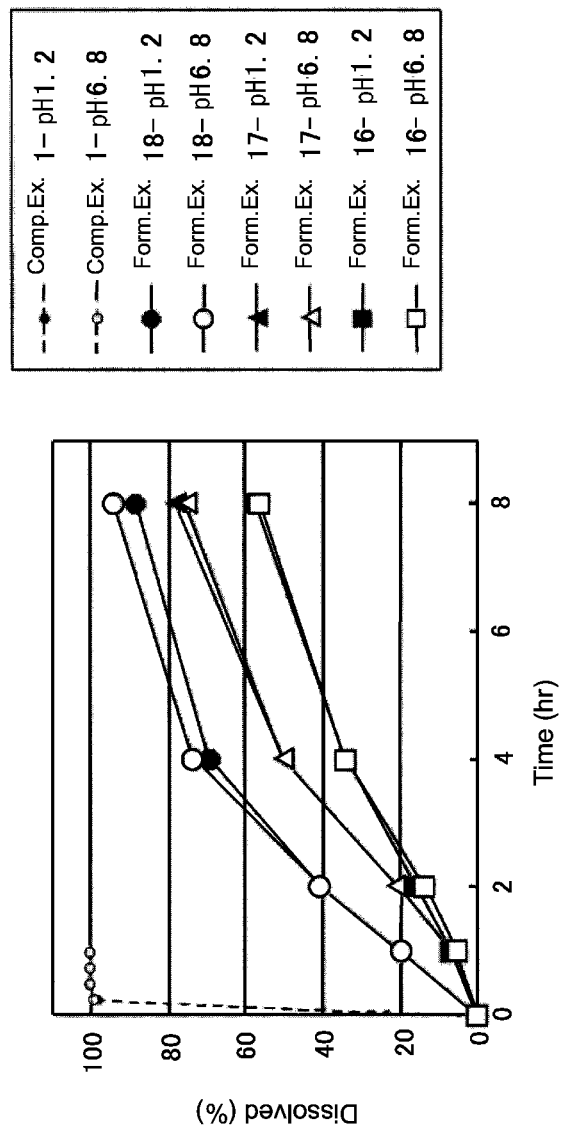
FIG. 2 is a graph showing the release profiles of compositions according to Comparative Example 1 (comp. ex.) and Formulation Examples 16-18 (form. ex.). In the drawings, filled symbols (•, ●, ▲, ■) show the states of elution in the second solution (pH 1.2), and open symbols (○,○,∆,□) show the states of elution in the second solution (pH 6.8).
Figure 3:
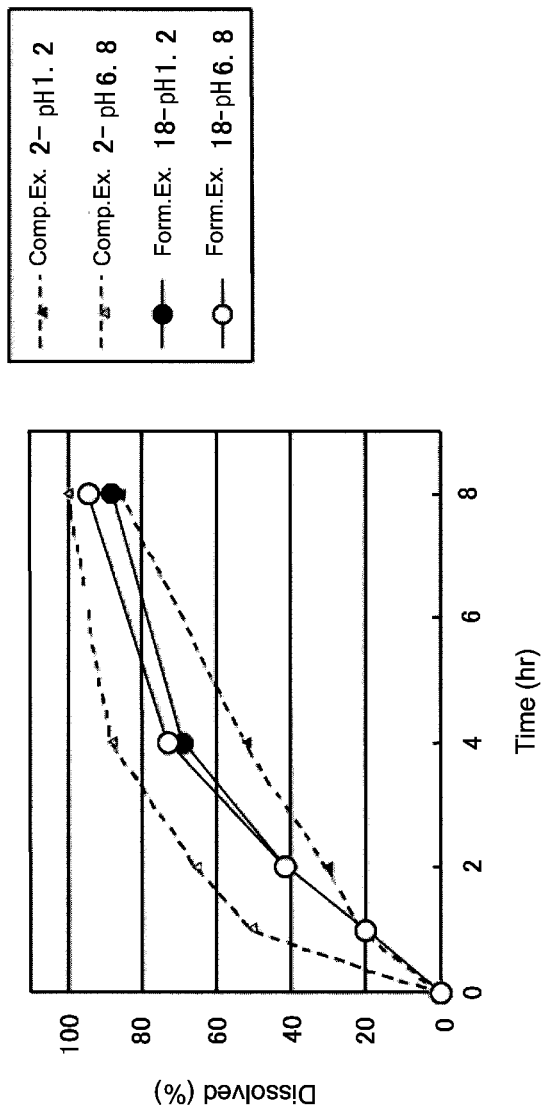
FIG. 3 is a graph showing the release profiles of compositions according to Comparative Example 2 (comp. ex.) and Formulation Examples 16 (form. ex.). In the drawings, filled symbols (•,▲) show the states of elution in the first solution (pH 1.2), and open symbols (○, ∆) show the states of elution in the second solution (pH 6.8).

They are shown in FIGS. 2 and 3.

As shown in FIG. 2, the preparations according to Formulation Examples 16, 17 and 18 showed sustained release in comparison with the immediate release preparation according to Comparative Example 1, and the release rate was able to be arbitrarily controlled by controlling the thicknesses of the coating layers. Further, as shown in FIG. 3, in case of the sustained release monolayered coating granules having a large particle size (not less than 1000 µm) as prepared in Comparative Example 2, fluctuation of release rate depending on the change in pH of the testing medium was observed due to the dissolution characteristics of beraprost sodium. In contrast, with the coating granules according to Formulation Examples 16-18 of the present invention, it was confirmed that stable release rate was able to be kept, which was not influenced by the fluctuation of the pH.

Test Example 2

Human Oral Absorption Test of Beraprost Sodium Preparations

It was proved in Test Example 1 that the sustained release beraprost sodium preparations according to the present invention attain stable continuous release irrespective of pH. To confirm the continuous release and absorption of beraprost sodium in vivo, oral absorption test was performed using human (healthy male adults), and drug level in plasma-time profile was evaluated.

Test Conditions

Subject: healthy male adults; Administration method: 120 µg/body (in terms of beraprost sodium) was administered once together with 50 ml of drinking water during fasting; Method for Measuring Plasma Drug Level: radioimmunoassay (RIA).

Figure 4:
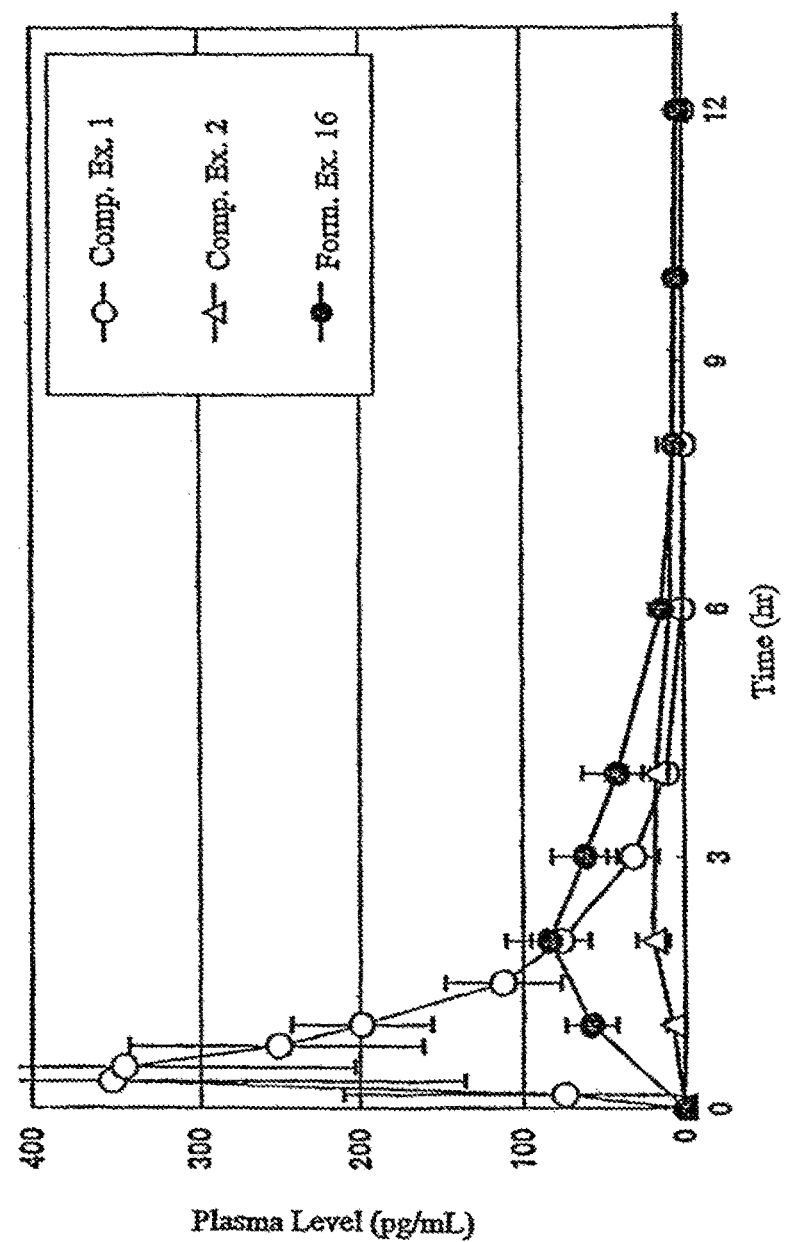
FIG. 4 shows plasma drug level-time profiles when the preparations according to Comparative Examples 1 and 2 (comp. ex.), and Formulation Example 16 (form. ex.) were orally administered to human.

The plasma level-time profile is shown in FIG. 4, and the drug kinetic parameters are shown in Table 4.

By administering the sustained release granules obtained in Formulation Example 16, the Tmax was delayed, and the blood level of the drug was sustained for a longer time when compared with the case where the immediate release tablet obtained in Comparative Example 1 was administered. By administering the sustained release granules obtained in Formulation Example 16, higher blood level was maintained than in the case where the sustained release monolayered coating granules having a large particle size (not less than 1000 µm) prepared in Comparative Example 2, so that better sustained release property and higher bioavailability were attained by the present invention. By these results, it was confirmed that the preparations according to the present invention move in the digestive tract keeping stable release rate in the entire digestive tract having a large pH fluctuation.

EFFECTS OF INVENTION

As is apparent from the in vitro dissolution tests and human oral absorption tests, it was confirmed that a sustained release preparation which is very preferred for stably releasing the drug in the entire digestive tract having a large pH fluctuation can be provided by coating the nucleus granule with skin constituted by a hot-melt low-melting substance layer and a layer containing the relatively water-insoluble macromolecular substance to prepare a relatively small sustained release coating granules. It was proved that a composition by which the blood level can be maintained at the therapeutic level for a long time and which has a good bioavailability can be obtained by using the method for attaining sustained release according to the present invention. This suggests the possibility for maintaining pharmacological effects and reducing side effects. Thus, the preparation according to the present invention is expected to be used for therapies of a variety of diseases as a highly safe and effective sustained release preparation.

The invention claimed is:

1. An oral sustained release pharmaceutical composition comprising:
   a plurality of granules having diameters of not more than 1000 µm,
   wherein said granules comprise:
   a nucleus granule comprised of beraprost sodium, and
   a coating agent comprising at least two skin layers of an outer layer and an inner layer which coat said nucleus granule, and
   wherein said outer layer comprises one or more relatively water-insoluble macromolecular substances selected from the group consisting of poly(ethylacrylate, methylmethacrylate), and poly(ethylacrylate, methylmethacrylate)trimethyl-ammonio-ethylmethacrylate chloride, and
   wherein said inner layer comprises a hot-melt low-melting substance selected from the group consisting of stearic acid, capric acid, lauric acid, myristic acid, palmitic acid, stearyl alcohol, myristyl alcohol, lauryl alcohol, cetyl alcohol, glyceryl palmitooleate, glyceryl monooleate, glyceryl monostearate, glyceryl monomyristate, glyceryl monobehenate, glyceryl trimyristate, glyceryl tribehenate, carnauba wax, and paraffins, wherein said composition provides a pH-independent release of said beraprost sodium.

2. The oral sustained release pharmaceutical composition of claim 1, wherein a weight ratio of said first skin layer to said second skin layer ranges from about 1:9 to about 9:1.

3. The oral sustained release pharmaceutical composition of claim 2, wherein said weight ratio ranges from about 3:7 to about 7:3.

4. The oral sustained release pharmaceutical composition of claim 1,
wherein said inner layer comprises a hot-melt low-melting substance selected fromm the group consisting of glyceryl palmitooleate, glyceryl monooleate, glyceryl monostearate, glyceryl monomyristate, glyceryl monobehenate, glyceryl trimyristate, and glyceryl tribehenate.

* * * * *

UNITED STATES PATENT AND TRADEMARK OFFICE
CERTIFICATE OF CORRECTION

PATENT NO. : 9,616,071 B2
APPLICATION NO. : 10/556641
DATED : April 11, 2017
INVENTOR(S) : Sandrine Salle et al.

It is certified that error appears in the above-identified patent and that said Letters Patent is hereby corrected as shown below:

On the Title Page

Insert:
--(30) Foreign Application Priority Data
May 20, 2003 (EPO) .......................... 03291180.2--

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*